United States Patent
Lee et al.

(10) Patent No.: US 8,781,310 B2
(45) Date of Patent: Jul. 15, 2014

(54) COATING COMPOSITION COMPRISING PHOTOCATALYST COATED WITH APATITE AND RADIANT HEATING SYSTEM

(75) Inventors: Kwang Seong Lee, Incheon (KR); Dong Ryol Hur, Incheon (KR); Jang Mok Lee, Seoul (KR)

(73) Assignee: Energy Korea Inc. (KR)

( * ) Notice: Subject to any disclaimer, the term of this patent is extended or adjusted under 35 U.S.C. 154(b) by 774 days.

(21) Appl. No.: 13/000,816

(22) PCT Filed: Aug. 6, 2008

(86) PCT No.: PCT/KR2008/004559
§ 371 (c)(1),
(2), (4) Date: Dec. 22, 2010

(87) PCT Pub. No.: WO2009/157612
PCT Pub. Date: Dec. 30, 2009

(65) Prior Publication Data
US 2011/0129204 A1     Jun. 2, 2011

(30) Foreign Application Priority Data
Jun. 24, 2008  (KR) ..................... 10-2008-0059536

(51) Int. Cl.
*H05B 3/20*     (2006.01)
*F24H 9/00*     (2006.01)

(52) U.S. Cl.
USPC ..................... 392/438; 392/432; 392/435

(58) Field of Classification Search
None
See application file for complete search history.

(56) References Cited

U.S. PATENT DOCUMENTS

| | | | |
|---|---|---|---|
| 5,981,425 A | 11/1999 | Taoda et al. | |
| 7,521,084 B2 * | 4/2009 | Nonami | 427/212 |
| 2004/0254267 A1 * | 12/2004 | Nagae | 523/333 |
| 2005/0175788 A1 * | 8/2005 | Nonami | 427/430.1 |
| 2009/0094954 A1 * | 4/2009 | Nakayama et al. | 55/524 |

FOREIGN PATENT DOCUMENTS

| | | |
|---|---|---|
| KR | 10-0506333 B1 | 7/2005 |
| KR | 20-0412829 Y1 | 3/2006 |
| KR | 10-2006-0100505 A | 9/2006 |
| KR | 10-2006-0119663 | 11/2006 |

* cited by examiner

*Primary Examiner* — Thor Campbell
(74) *Attorney, Agent, or Firm* — David R. Stevens; Stevens Law Group (57) ABSTRACT

A photocatalytic coating composition is provided. The composition comprises a hydroxyapatite-coated photocatalyst, a silica-based binder, an acrylic emulsion, a thickener and water. Further provided is a radiant heating system having the composition. The system has deodorizing and antibacterial properties.

4 Claims, 10 Drawing Sheets

KICM

KOREA INSTITUTE OF CONSTRUCTION MATERIALS

Add. : 137-707 1465-4, Seocho 3-dong, Seocho-gu, Seoul, Korea
Tel. : (02)3415-8881   FAX : (02)3415-8877   URL : www.kicm.re.kr

Certificate of Testing(Inspection) Result

| | |
|---|---|
| Samplet No. of Issue | F I D - 0 3 7 |
| Name of Applicant | Kwang Seong, Lee [Energy Korea Inc.] |
| Address of Applicant | BLDG, "C", #1008, Woolim Lion's Valley, 425, Cheongcheon-Dong, Incheon, Korea |
| Date of Receipt | May. 23, 2008 |
| Name of Test Sample | Far Infrared Radiation Heating Panel for Air-cleaning |

Result of Testing

| Test Item | Test Result | Test Method |
|---|---|---|
| The removal ratio of $CH_3CHO$ (%) | N. D. (99<) | Provided by Customer |

1. N. D. : Non-detected or less than the lowest detecting limit(0.25 ppm).
2. 99< : The removal ratio of $CH_3CHO$ is more than 99 %.          End.

※ Object of Test : Quality Management
1. This test report is the result of testing specimen and the name of sample provided by the applicant. But we do not guarantee the quality of entire product.
2. This test report is not able to be used by public relation, advertisement, lawsuit without consent with KICM and this is not used except original purpose.
3. The term of duplicate's issue is a half year from the date of issue. And the manuscript is invalidated.

| Jun. | 17 | 2008 |
|---|---|---|
| month | day | year |

Signed  *Jang Mok Lee*

The general manager of Korea
Institute of Construction Materials

Fig. 3

KICM
KOREA INSTITUTE OF CONSTRUCTION MATERIALS

Add. : 137-707  1465-4, Seocho 3-dong, Seocho-gu, Seoul, Korea
Tel. : (02)3415-8881    FAX : (02)3415-8877    URL : www.kicm.re.kr

Certificate of Testing(Inspection) Result

| | | |
|---|---|---|
| Sample/ No. of Issue | : | P I D - 0 3 9 |
| Name of Applicant | : | Kwang Seong, Lee [Energy Korea Inc.] |
| Address of Applicant | : | BLDG, "C", #1003, Woolim Lion's Valley, 425, Cheongcheon-Dong, Incheon, Korea |
| Date of Receipt | : | May, 23. 2008 |
| Name of Test Sample | : | Far Infrared Radiation Heating Panel for Air-cleaning |

Result of Testing

| Test Item | Test Result | Test Method |
|---|---|---|
| The removal ratio of $NH_3$ (%) | 9 | Provided by Customer |

End.

※ Object of Test : Quality Management.
1. This test report is the result of testing specimen and the name of sample provided by the applicant. But we do not guarantee the quality of entire product.
2. This test report is not able to be used by public relation, advertisement, lawsuit without consent with KICM and this is not used except original purpose.
3. The term of duplicate's issue is a half year from the date of issue. And the manuscript is invalidated.

| Jun. | 17 | 2008 |
|---|---|---|
| month | day | year |

Signed  Jang Mok Lee

The general manager of Korea
Institute of Construction Materials

Fig. 4

KICM
KOREA INSTITUTE OF CONSTRUCTION MATERIALS

Add. : 137-707 1465-4, Seocho 3-dong, Seocho-gu, Seoul, Korea
Tel. : (02)3415-8881   FAX : (02)3415-8877   URL : www.kicm.re.kr

Certificate of Testing(Inspection) Result

| | |
|---|---|
| Sample No. of Issue | : F I D - 0 3 6 |
| Name of Applicant | : Kwang Seong, Lee [Energy Korea Inc.] |
| Address of Applicant | : BLDG, "C", #1003, Woolim Lion's Valley, 425, Cheongcheon-Dong, Incheon, Korea |
| Date of Receipt | : May. 23. 2008 |
| Name of Test Sample | : Far Infrared Radiation Heating Panel for Air-cleaning |

Result of Testing

| Test Item | Test Result | Test Method |
|---|---|---|
| The removal ratio of $CH_3CHO$ (%) | N. D. (99<) | PRKS L-002 |

1. N. D. : Non-detected or less than the lowest detecting limit(0.25 ppm).
2. 99< : The removal ratio of $CH_3CHO$ is more than 99 %.     End.

※ Object of Test : Quality Management
1. This test report is the result of testing specimen and the name of sample provided by the applicant. But we do not guarantee the quality of entire product.
2. This test report is not able to be used by public relation, advertisement, lawsuit without consent with KICM and this is not used except original purpose.
3. The term of duplicate's issue is a half year from the date of issue. And the manuscript is invalidated.

| Jun. | 17 | 2008 |
|---|---|---|
| month | day | year |

Signed  *Jang Mok Lee*

The general manager of Korea
Institute of Construction Materials 2-1

Fig. 5

KICM

KOREA INSTITUTE OF CONSTRUCTION MATERIALS

Add. : 137-707  1465-4, Seocho 3-dong, Seocho-gu, Seoul, Korea
Tel. : (02)3415-8881    FAX : (02)3415-8877    URL : www.kicm.re.kr

Certificate of Testing(Inspection) Result

| | |
|---|---|
| Sample No. of Issue | : F I D - 0 3 8 |
| Name of Applicant | : Kwang Seong, Lee [Energy Korea Inc.] |
| Address of Applicant | : BLDG, "C", #1003, Woolim Lion's Valley, 425, Cheongcheon-Dong, Incheon, Korea |
| Date of Receipt | : May. 23. 2008 |
| Name of Test Sample | : Far Infrared Radiation Heating Panel for Air-cleaning |

Result of Testing

| Test Item | Test Result | Test Method |
|---|---|---|
| The removal ratio of $NH_3$ (%) | N. D. (99<) | Provided by Customer |

1. N. D. : Non-detected or less than the lowest detecting limit(0.25 ppm)
2. 99< : The removal ratio of $NH_3$ is more than 99 %.    End.

※ Object of Test : Quality Management
1. This test report is the result of testing specimen and the name of sample provided by the applicant. But we do not guarantee the quality of entire product.
2. This test report is not able to be used by public relation, advertisement, lawsuit without consent with KICM and this is not used except original purpose.
3. The term of duplicate's issue is a half year from the date of issue. And the manuscript is invalidated.

Jun.    17    2008
month    day    year

Signed  Jong Mok Lee

The general manager of Korea
Institute of Construction Materials 2-1

Fig. 6

KICM

KOREA INSTITUTE OF CONSTRUCTION MATERIALS
(THE CENTER OF WELLBEING MATERIALS)
Add. : 1465-4, Seocho-3Dong, Seocho-Ku, Seoul, Korea
Tel. : 3415-8880~81, URL : www.kicm.re.kr

Certificate of Testing Result

| | |
|---|---|
| Serial No. of Issue | : R080523 - FW006 |
| Name of Applicant | : Kwang Seong, Lee [Energy Korea Inc.] |
| Address of Applicant | : BLDG. "C", #1003, Woolim Lion's Valley, 425, Cheongcheon-Dong, Incheon, Korea |
| Date of Receipt | : May. 23, 2008 |
| Name of Test Sample | : Far Infrared Radiation Heating Panel for Air-cleaning |

Result of Testing

| Item of test | | Result of Testing | | | Test Method |
|---|---|---|---|---|---|
| | | Early Conc. (CFU/100p) | After 2hr.Conc. (CFU/100p) | Reduction rate of bacteria(%) | |
| Antibacterial test for *Escherichia coli* | BLANK | 2370 | 2370 | - | Client's requirement method |
| | Far Infrared Radiation Heating Panel for Air-cleaning | 2370 | 2 | 99.9 | |
| Antibacterial test for *Staphylococcus aureus* | BLANK | 2226 | 2226 | - | |
| | Far Infrared Radiation Heating Panel for Air-cleaning | 2226 | 2 | 99.9 | |
| Antibacterial test for *Salmonella typhimurium* | BLANK | 2279 | 2279 | | |
| | Far Infrared Radiation Heating Panel for Air-cleaning | 2279 | 2 | 99.9 | |

End.

※ Name of test bacteria
*Escherichia coli* ATCC 25922
*Staphylococcus aureus* ATCC 6538
*Salmonella typhimurium* IFO 14193

※ Refer to the enclosed
※ Object of Test : Quality Control
1. This Test Report is the result of testing specimen and the name of sample provided by the applicant. But we do not guarantee the quality of entire product.
2. This Test Report is not able to by public relation, advertisement, lawsuit without consent with KICM and this is not used except original purpose.
3. The term of duplicate's issue is a half year from the date of issue. And the manuscript is invalidated.

Jun. 18 2008
month day year

Signed

The general manager of Korea
Institute of Construction Materials

COATING COMPOSITION COMPRISING PHOTOCATALYST COATED WITH APATITE AND RADIANT HEATING SYSTEM

TECHNICAL FIELD

The present invention relates to a coating composition comprising a photocatalyst coated with apatite and a radiant heating system having the same.

BACKGROUND ART

A photocatalyst is a substance that absorbs light of a predetermined wavelength band to assist in causing a chemical reaction to take place. For example, a photocatalyst completely oxidizes a toxic substance to carbon dioxide and water using an oxidizing agent (e.g., oxygen or water) under light irradiation.

Since the late 1980's, considerable research has been concentrated on photocatalytic oxidation reactions utilizing photocatalysts as advanced oxidation processes in developed countries. In a typical photocatalytic oxidation reaction, hydroxyl radicals and superoxides are created as intermediates to oxidize organic pollutants. A major advantage of photocatalytic oxidation reactions is that only oxygen can be supplied to sufficiently decompose organic pollutants without the addition of an additional oxidant, such as hydrogen peroxide or ozone, and sterilizing effects can be attained.

Photocatalysts are widely used for the purpose of decomposing pollutants in various industrial fields. In Japan, numerous photocatalytic products capable of decomposing a variety of harmful organic substances are currently being developed and commercialized. For example, photocatalysts are applied to concrete and building exterior materials (e.g., tiles) to maintain the concrete and building surfaces clean for at least ten years. Conventional photocatalytic products are very effective in decomposing organic pollutants but do not sufficiently exert their peculiar performance under conditions protected from light, particularly in a UV-deficient environment, such as indoor. Accordingly, when conventional photocatalytic products are applied to interior products, the performance of the photocatalytic products is greatly reduced.

Korean Patent Application No. 10-2000-0059193 A (Oct. 9, 2000) discloses a packing material for a cooling tower that uses a sterilizing photocatalyst to achieve semi-permanent sterilizing effects, thus eliminating the need for the periodic addition and management of sterilizing agents without causing pollution of cooling water and adversely affecting the equipment.

Korean Patent Application No. 10-2000-0045311 A (Aug. 4, 2000) discloses a water purification system that uses a rotary member having a film coated with titanium oxide as a photocatalyst.

Korean Patent Application No. 10-2000-0035845 A (Jun. 28, 2000) discloses a water purification pot that uses UV light and titanium dioxide as a photocatalyst to purify water in the pot.

Japanese Unexamined Patent Publication No. 2008-105905 (May 8, 2008) discloses a water photolysis system using a photocatalyst.

Japanese Unexamined Patent Publication No. 2008-094709 (Apr. 24, 2008) discloses a photocatalytic mortar admixture for a building that is capable of purifying organic substances.

U.S Patent Publication No. 2007-0297973 (Dec. 27, 2007) discloses a method for preparing a photocatalyst.

U.S Patent Publication No. 2006-0159598 (Jul. 20, 2006) discloses an air purifier using a photocatalyst.

DISCLOSURE OF INVENTION

Technical Problem

Conventional photocatalytic compositions are very effective in decomposing organic pollutants in the UV region but do not sufficiently exert their peculiar performance under conditions protected from light, particularly indoors. That is, when conventional photocatalysts are applied to interior products, the inherent performance characteristics (e.g., pollutant decomposition and sterilization) of the photocatalysts are not satisfactorily exhibited.

Thus, there is a need to develop a photocatalytic coating composition that is suitably applicable to interior products as well as exterior products.

Photocatalysts may decompose supports (or carriers) due to their high oxidizing activity. Photocatalysts absorb UV light to produce hydroxyl radicals or superoxides, which decompose supports into water and carbon dioxide. This decomposition causes the photocatalysts to be separated from the supports, leading to a deterioration in the performance of photocatalytic products.

Thus, there is a need to develop a photocatalytic coating composition that can minimize the separation of a photocatalyst from a support.

On the other hand, prior art radiant heating systems have no ability to purify malodorous ingredients in indoor air. Heating of a room using a prior art radiant heating system activates molecules of cigarette smoke and malodorous ingredients in the room so that people feel the indoor air more malodorous. Further, an increase in indoor temperature by heating provides a favorable environment for bacterial proliferation. In conclusion, since prior art radiant heating systems have no ability to purify indoor air, the indoor air becomes more malodorous and bacteria grow faster therein.

Thus, there is a need to develop a radiant heating system that is capable of purifying indoor air.

Technical Solution

The present invention has been made in an effort to solve the above problems of the prior art, and it is one object of the present invention to provide a photocatalytic coating composition that can be applied to interior products as well as exterior products due to its high photocatalytic performance even in the visible region.

It is another object of the present invention to provide a radiant heating system having the photocatalytic coating composition to purify indoor air.

In accordance with one aspect of the present invention, there is provided a photocatalytic coating composition comprising 5 to 20% by weight of a hydroxyapatite-coated photocatalyst, 5 to 15% by weight of a silica-based binder, 1 to 5% by weight of an acrylic emulsion, 0.1 to 1% by weight of a thickener and 54 to 85% by weight of water.

The hydroxyapatite-coated photocatalyst preferably has a coverage ratio in the range of 5 to 36%.

The hydroxyapatite-coated photocatalyst preferably has an average particle diameter in the range of 1 to 250 nm.

The photocatalyst is preferably selected from titanium dioxide, zinc oxide, zirconium oxide, tin oxide, vanadium trioxide and combinations thereof.

The thickener is preferably xanthan gum.

The photocatalytic coating composition of the present invention is preferably used for the manufacture of a radiant heating system.

In accordance with another aspect of the present invention, there is provided a radiant heating system having the photocatalytic coating composition.

Specifically, the radiant heating system of the present invention comprises a substrate, a heating layer and a radiant heat-emitting layer.

The substrate is preferably a stainless steel (SUS) or aluminum plate.

The heating layer is preferably formed of at least nickel-chromium wire coated with silicone, Teflon or glass yarn.

The radiant heat-emitting layer is preferably formed by applying a mixture of a radiant inorganic material, 20 to 25% by weight of an alkoxy silane adhesive and 10 to 15% by weight of an alcoholic solvent to the substrate and drying the solvent, the radiant inorganic material being composed of 6 to 12% by weight of $TiO_2$, 20 to 30% by weight of $SiO_2$, 5 to 10% by weight of $ZrO_2$, 5 to 10% by weight of $Al_2O_3$, 5 to 10% by weight of $Fe_2O_3$, 5 to 10% by weight of $MnO_2$ and 1 to 5% by weight of $Na_2O$.

The radiant heating system of the present invention further comprises a heat-insulating layer on an outermost surface thereof opposed to the surface of the radiant heat-emitting layer.

The heat-insulating layer is preferably formed of glass fiber and has a thickness in the range of 15 to 25 mm.

The radiant heating system of the present invention further comprises an irregular surface layer on the surface of the radiant heat-emitting layer.

The irregular surface layer is preferably formed by coating a supersaturated aqueous solution of a mixture of $SiO_2$ and $CaO_2$ on the surface of the radiant heat-emitting layer and drying the water.

The irregular surface layer is preferably formed by coating a supersaturated aqueous solution of a mixture of $SiO_2$ and $CaO_2$ in a weight ratio of 1:4 on the surface of the radiant heat-emitting layer and drying the water.

The radiant heating system of the present invention further comprises a photocatalytic coating layer.

The photocatalytic coating layer preferably has a thickness in the range of 30 to 300 μm.

In accordance with another aspect of the present invention, there is provided a method for manufacturing the radiant heating system, the method comprising the steps of applying the photocatalytic coating composition to the radiant heat-emitting layer and curing the surface of the radiant heat-emitting layer in the temperature range of 18 to 150° C.

In accordance with yet another aspect of the present invention, there is provided a method for manufacturing the radiant heating system, the method comprising the steps of applying the photocatalytic coating composition to the irregular surface layer and curing the surface of the irregular surface layer in the temperature range of 18 to 150° C.

Before describing the present invention, terms used herein are defined as follows.

The term 'coating material' is a generic term for fluid materials, such as paints and enamels, that are coated on the surfaces of solid materials to form solid films. The coating material protects the surfaces of the solid materials or renders the surfaces aesthetically pleasing. The coating material is in a fluid state, such as gel, before and during coating. It is preferable to dry and cure the coating material immediately after coating.

The term 'apatite' refers to a material that has the ability to adsorb organic substances and bacteria and is represented by $Ca_x(PO_4)_y(OH)_z$ [x=5z, y=3z and z=1~50]. A representative example of apatite is hydroxyapatite whose molecular formula is $Ca_{10}(PO_4)_6(OH)_2$.

The term 'coverage ratio' is defined as a value obtained by calculating the ratio of the surface area of a first material adsorbed or occupied by a second material to the entire surface area of the first material, and multiplying the ratio by 100.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Preferred embodiments of the present invention will now be described in detail.

The present invention provides a photocatalytic coating composition comprising 5 to 20% by weight of a hydroxyapatite-coated photocatalyst, 5 to 15% by weight of a silica-based binder, 1 to 5% by weight of an acrylic emulsion, 0.1 to 1% by weight of a thickener and 54 to 85% by weight of water, based on the total weight of the composition.

The hydroxyapatite-coated photocatalyst is a very important component of the photocatalytic coating composition. Conventional photocatalysts tend to be separated from their supports (or carriers) with the passage of time because they decompose the supports as well as pollutants. In contrast, the apatite-coated photocatalyst used in the photocatalytic coating composition of the present invention keeps the photocatalyst from being in direct contact with apatite as a support to prevent the photocatalyst from being separated from the support. Further, the apatite improves the ability to adsorb pollutants due to its porous structure to allow the photocatalyst to efficiently decompose the pollutants.

The photocatalyst may be selected from titanium dioxide, zinc oxide, zirconium oxide, tin oxide, vanadium trioxide and combinations thereof. Titanium dioxide is preferred because of its high photocatalytic activity. It is known that the photocatalytic activity of the photocatalysts increases in the order: titanium dioxide>zinc oxide>zirconium oxide>tin oxide>vanadium oxide.

The hydroxyapatite-coated photocatalyst is preferably added in an amount of 5 to 20% by weight, based on the total weight of the composition. If the hydroxyapatite-coated photocatalyst is added in an amount of less than 5% by weight, it is difficult for the photocatalyst to exert beneficial effects, such as antibacterial activity, antifungal activity, deodorizing effects and indoor air quality improvement. Meanwhile, when the hydroxyapatite-coated photocatalyst is added in an amount of more than 20% by weight, the use of the expensive photocatalyst increases, which is economically disadvantageous.

The coverage ratio of the hydroxyapatite relative to the surface of the photocatalyst is preferably between 5% and 36%. When the coverage ratio is lower than 5%, the ability of the hydroxyapatite to adsorb pollutants is unsatisfactory and the photocatalyst may be separated from the support. Meanwhile, when the coverage ratio exceeds 36%, the hydroxyapatite covers a large portion of the photocatalyst, resulting in damage to the performance of the photocatalyst.

The average particle diameter of the apatite-coated photocatalyst is preferably in the range of 1 to 250 nm. When the apatite-coated photocatalyst has an average particle diameter smaller than 1 nm, the applicability of the photocatalyst to a coating material is negligible and the ability of the photocatalyst to receive light is significantly reduced. When the photocatalyst has an average particle diameter larger than 250 nm, it is difficult to disperse the photocatalyst particles in water, which makes it nearly impossible to prepare a coating material in which the photocatalyst is homogeneously dispersed.

The silica-based binder is highly miscible with the photocatalyst. The silica-based binder serves to block aggregation of the hydroxyapatite-coated photocatalyst particles and disperse titanium dioxide particles as the photocatalyst particles in water. To this end, the silica-based binder is preferably added in an amount of 5 to 15% by weight, based on the total weight of the composition. The use of the silica-based binder in an amount of less than 5% by weight may cause the photocatalyst particles to aggregate. Meanwhile, the use of the silica-based binder in an amount of more than 15% by weight blocks the surface of the apatite-coated photocatalyst to deteriorate the photocatalytic activity of the photocatalyst.

The acrylic emulsion is an auxiliary binder. The acrylic emulsion serves to allow the apatite-coated photocatalyst and the silica-based binder to be well seated on the surface of a radiant heating system, which will be described below. The content of the acrylic emulsion is preferably in the range of 1 to 5% by weight, based on the total weight of the composition. The use of the acrylic emulsion outside the content range defined above adversely affects the fixation and photocatalytic activity of the photocatalyst.

The thickener is a component that imparts viscosity to the other components and is preferably xanthan gum. The content of the thickener is preferably in the range of 0.1 to 1% by weight, based on the total weight of the composition. Out of this range, the viscosity of the composition becomes too low or too high, which adversely affects the flowabilty and workability of the composition.

From the viewpoint of economic efficiency, activity of the titanium dioxide, viscosity of the coating material and coating processability, the water is preferably present in an amount of 54 to 85% by weight, based on the total weight of the composition.

A method for coating the photocatalytic coating composition of the present invention will be explained hereinbelow.

The photocatalytic coating composition of the present invention can be coated on various substrates by spray coating, dip coating and roll coating. Examples of such substrates include concrete, wood and plastic substrates.

The photocatalytic coating composition is coated on a radiant panel of a radiant heating system by one of the coating processes to form a coating film. It is preferable to cure the coated radiant panel in the temperature range of 18 to 150° C. A curing temperature lower than 18° C. lowers the hardness of the coating film. Meanwhile, a curing temperature higher than 150° C. increases the risk that the coating film may be split due to the rapid curing.

The present invention also provides a radiant heating system having the photocatalytic coating composition.

The radiant heating system of the present invention is intended to include those that use the photocatalytic coating composition and comprise a radiant heat-emitting material and a heating unit, and no particular limitation is imposed on the types of the radiant heat-emitting material and the heating unit. In an embodiment, the radiant heating system has high far-infrared radiation efficiency.

The radiant heating system uses the photocatalytic coating composition and comprises a substrate, a heating layer and a radiant heat-emitting layer. The photocatalytic coating composition is homogeneously mixed in the radiant heat-emitting layer or is used to form a photocatalytic coating layer. The radiant heating system may further comprise a heat-insulating layer.

Figure 1:
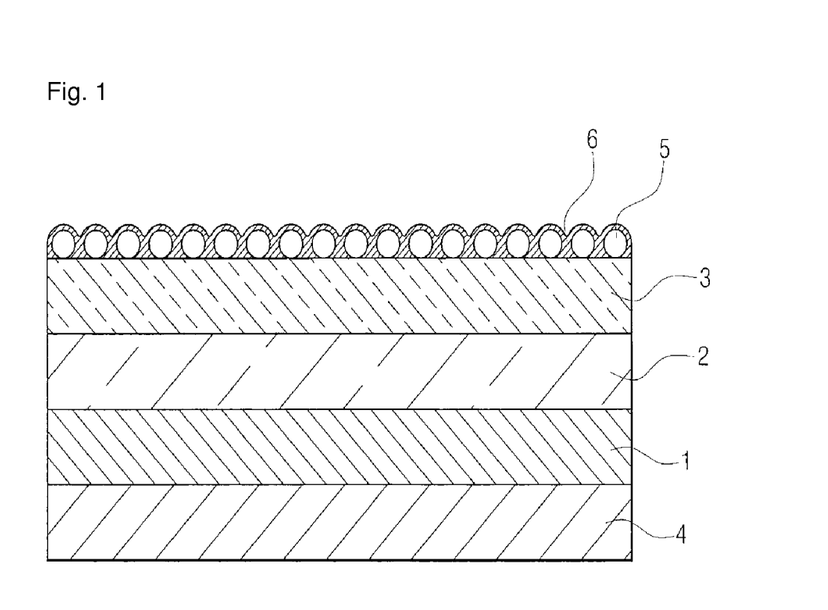
FIG. 1 shows the structure of a radiant heating system according to an embodiment of the present invention.

FIG. 1 shows the structure of a radiant heating system according to another embodiment of the present invention. Specifically, the radiant heating system comprises a substrate 2, a heating layer 1, a radiant heat-emitting layer 3, a heat-insulating layer 4, an irregular surface layer 5 and a photocatalytic coating layer 6.

The radiant heat-emitting layer 3 can be formed of at least one inorganic material selected from $TiO_2$, $SiO_2$, $ZrO_2$, $Al_2O_3$, $Fe_2O_3$, $MnO_2$, $2MgO.2Al_2O_3.5SiO_2$ and $Al_2O_3.TiO_2$. Preferably, the inorganic material is selected from the group consisting of $TiO_2$, $SiO_2$, $ZrO_2$, $Al_2O_3$, $Fe_2O_3$, $MnO_2$ and $Na_2O$. These organic materials may be used alone or as a mixture thereof.

Particularly, the radiant heat-emitting layer 3 is preferably formed by applying a mixture of a radiant inorganic material, 20 to 25% by weight of an alkoxy silane adhesive and 10 to 15% by weight of an alcoholic solvent to the substrate 2 and drying the solvent. The radiant inorganic material is composed of 6 to 12% by weight of $TiO_2$, 20 to 30% by weight of $SiO_2$, 5 to 10% by weight of $ZrO_2$, 5 to 10% by weight of $Al_2O_3$, 5 to 10% by weight of $Fe_2O_3$, 5 to 10% by weight of $MnO_2$ and 1 to 5% by weight of $Na_2O$. The radiant heat-emitting layer 3 can emit radiant heat electromagnetic waves whose wavelength is in the range of 2.5 to 25 μm (central wavelength: 9 μm), which are known to be highly transmissive, at a temperature of about 92° C. to about 110° C.

The material for the radiant heat-emitting layer 3 is preferably very pure and has a large particle size, e.g., at least 350 mesh.

The radiant heat-emitting layer 3 can be formed by mixing the inorganic material with the adhesive and the solvent, applying the mixture to one surface of the substrate 2, and drying the mixture. The adhesive is a material that has high heat conductivity and excellent heat resistance. Specifically, the adhesive is thermally stable at 250° C. or above, preferably 300° C. or above. Any known adhesive material may be used herein, and examples thereof include acrylic resins and epoxy resins. As the solvent, a ketone-based solvent can be used.

In an alternative embodiment, a radiant heating system can be manufactured by mixing the material for the radiant heat-emitting layer 3 with the photocatalytic coating composition and drying the mixture. Although the radiant heating system is effective in purifying air, it exhibits slightly poor photocatalytic activity when compared to the radiant heating system comprising the photocatalytic coating layer 6 formed having the photocatalytic coating composition.

The substrate 2 plays a role in supporting the radiant heat-emitting layer 3 and the heating layer 1. There is no particular restriction on the kind of the substrate material. The substrate 2 may be a synthetic resin, stainless steel (also known as 'SUS' to those skilled in the art) or aluminum plate. Particularly, the substrate is made of a material that is highly heat resistant, undergoes no variation in chemicophysical properties in the temperature range of 92 to 250° C., and preferably has a coefficient of thermal expansion similar to the adjacent layers, i.e. the heating layer 1 and the radiant heat-emitting layer 3. The substrate is preferably made of a material that has high heat conductivity and a low specific gravity to assist in reducing the weight of the radiant heating system. The system of the present invention can be positioned on the ceiling or wall. The system of the present invention may be attached to a support structure. Thus, a reduction in the weight of the system according to the present invention is considered as being an important factor. The substrate 2 is preferably an aluminum plate.

Any material may be used to form the heating layer 1 so long as it can generate heat when power is supplied from an external power source. Specifically, the heating layer 1 is preferably formed of a material that has little variation in resistance in response to temperature (that is, low resistance coefficient as a function of temperature), is highly flexible, and undergoes little variation in physicochemical properties. For example, a heat-emitting fine wire can be used to form the heating layer 1. If the heat-emitting fine wire has low mechanical strength or its surface tends to be oxidized to cause increased contact resistance, it may adversely affect the operation of the system according to the present invention.

For example, the heating layer 1 can be formed by coating at least heat-emitting wire (e.g., iron-chromium (Fe—Cr), nickel-chromium (Ni—Cr) or copper-nickel (Cu—Ni) wire) with a synthetic resin (e.g., polyfluoroethylene (Teflon, DuPont, U.S.A.), silicone or glass yarn, which is a kind of glass fiber widely known in the art) that is stable at a temperature as high as 300° C. The heat-emitting wire coated with the synthetic resin generates heat when power is supplied and transfers the heat to the radiant heat-emitting layer 3.

In the case where the radiant heating system of the present invention is installed in a desired space, the heat-insulating layer 4 may be disposed on an outermost surface of the system opposed to the surface of the radiant heat-emitting layer 3. In this case, the heat-insulating layer 4 blocks the radiation of the heat generated from the heating layer 1 toward the surface opposed to the surface of the radiant heat-emitting layer 3, so that the radiant heat can be efficiently emitted. Further, the heat-insulating layer 4 can block the heat generated from the heating layer 1 to reduce the risk of fire.

The heat-insulating layer 4 is preferably formed of a non-flammable and lightweight material, for example, a gypsum board or high-density glass fiber board. A high-density glass fiber board is particularly preferred because it is light in weight and causes few pollution problems. When it is intended to form the heat-insulating layer using a glass fiber board, the outer surfaces of the glass fiber board, through which glass fiber is exposed to the outside, may be covered with an adhesive-treated glass fiber fabric or a Vaporbarrier (which is a composite material of an aluminum foil, a PVC film, a fiber glass yarn, etc). Any heat-insulating material known in the art may be used without limitation. The thickness of the heat-insulating layer 4 may be appropriately determined by those skilled in the art, taking into consideration the total weight and volume of the system and other processes. Most preferably, the heat-insulating layer 4 has a thickness of about 15 nm to about 25 mm.

The heat-insulating layer 4 can be adhered to the heating layer 1 by means of an adhesive. In an alternative embodiment, the heat-insulating layer 4 may be assembled with the substrate 2 or the heating layer 1 without the use of an adhesive. For example, the heat-insulating layer 4, the heating layer 1, the substrate 2 and the radiant heat-emitting layer 3 may be fixed to an aluminum frame, thus eliminating the need to use an adhesive.

The irregular surface layer 5 may be disposed on the surface of the radiant heat-emitting layer 3 from which radiant heat is emitted. The irregular surface layer 5 is formed by roughening the surface of the radiant heating system from which radiant heat is emitted to increase the surface area from which radiant heat is emitted, leading to an increase in the radiation efficiency of the system. The temperature of the irregular surface layer 5 is slightly lower than that of the radiant heat-emitting layer 3. Therefore, although a user is in contact with the irregular surface layer 5, he/she can be protected from the danger of being burnt.

The irregular surface layer 5 may be formed of a mixture such that including silicon dioxide ($SiO_2$) and calcium dioxide ($CaO_2$). The irregular surface layer may be formed by coating a supersaturated aqueous solution of a mixture of $SiO_2$ and $CaO_2$ on the surface of the radiant heat-emitting layer and drying the water. The degree of supersaturation of the supersaturated aqueous solution is not particularly limited so long as the dioxides can be homogeneously distributed on the surface of the radiant heat-emitting layer 3. The texture of the dioxide particles remains unchanged to roughen the surface of the system and increase the surface area. That is, the irregularities of the surface layer 5 increase the outermost surface area of the system, eventually resulting in an increase in emissivity. At this time, the ratio of the $SiO_2$ to the $CaO_2$ in the supersaturated aqueous solution may be appropriately adjusted. From the standpoint of high emissivity and smooth coating, it is most preferred to adjust the weight ratio of the $SiO_2$ to the $CaO_2$ to 1:4.

The photocatalytic coating layer 6 may be formed by applying the photocatalytic coating composition to the radiant heat-emitting layer 3. In an alternative embodiment, the photocatalytic coating layer 6 may be formed by applying the photocatalytic coating composition to the irregular surface layer 5. The photocatalytic coating composition is transparent enough for radiant heat (e.g., far-infrared rays) to penetrate therethrough even after being cured and dried. Accordingly, the influence of the photocatalytic coating layer 6 on the far-infrared radiation efficiency of the radiant heating system is minimized. If the photocatalytic coating layer 6 is formed too thick, the far-infrared radiation efficiency of the radiant heating system may be negatively affected. In view of this, the thickness of the coating layer is preferably in the range of 30 to 300 μm and more preferably 30 to 150 μm.

The photocatalytic coating layer 6 has the same shape as the substrate to minimize the influence on the radiant heat emission efficiency of the system. For example, as shown in FIG. 1, the photocatalytic coating layer 6 is formed so as to correspond to the irregularities of the surface layer 5, and as a result, the influence of the photocatalytic coating layer 6 on the radiant heat emission efficiency of the system is minimized. The photocatalytic coating composition of the present invention has a viscosity appropriate for forming the photocatalytic coating layer 6.

The size of the system according to the present invention may be determined by those skilled in the art according to the final applications and process conditions. Further, the respective constituent layers of the system are not required to have the same size. The sizes of the constituent layers may vary so long as the functions of the layers are not impaired.

MODE FOR THE INVENTION

Hereinafter, the present invention will be explained in more detail with reference to the following examples. However, these examples are given for the purpose of illustration and are not intended to limit the present invention.

EXAMPLES

Preparation of Hydroxyapatite-Coated Photocatalyst

First, a simulated body fluid of hydroxyapatite was obtained by mixing $Na^+$ (213 mM), $K^+$ (7.5 mM), $Ca^{2+}$ (50 mM), $Mg^{2+}$ (1.5 mM), $Cl^-$ (147.8 mM), $HCO_3^-$ (6 mM), $HPO_4^{2-}$ (12 mM) and $SO_4^{2-}$ (0.75 mM) in water.

Titanium dioxide was dispersed in the simulated body fluid while rotating at high speed and stirred for one hour. As a result, hydroxyapatite was uniformly seated on the surface of the titanium dioxide. After the stirring was stopped, the hydroxyapatite was allowed to grow for 24 hours to prepare the titanium dioxide uniformly coated with the hydroxyapatite. The hydroxyapatite-coated titanium dioxide was stabilized by heating at 200-300° C. for one hour.

The titanium dioxide may be of any type selected from anatase, rutile and brookite types. In this example, anatase type titanium dioxide (P25, Degussa, Germany) was used as the photocatalyst.

Preparation of Photocatalytic Coating Composition

An aqueous solution of the hydroxyapatite-coated titanium dioxide was mixed with a silica binder and an acrylic emulsion, followed by slow stirring. Thereafter, xanthan gum as a thickener was added to the mixture and rapidly stirred to prepare a photocatalytic coating composition.

The silica binder was prepared by dispersing a silane in an alcohol, slowly adding water to the dispersion with stirring and allowing the mixture to hydrate for 24-48 hours to prepare silica. At this time, the water was used in an amount of 10-20 parts by weight with respect to 100 parts by weight of the silane.

The photocatalytic coating composition was cured to cyclize the silica with the titanium dioxide. This cyclization led to an ideal state in which only air was allowed to pass through the layer while blocking moisture from entering from the outside.

Application of Photocatalytic Coating Composition and Manufacture of Radiant Heating System The photocatalytic coating composition was applied to the radiant heat-emitting layer 3 or the irregular surface layer 5 by a coating process selected from spray coating, dip coating, roll coating and brush coating. Following the application, the photocatalytic coating composition was cured in the temperature range of 18-150° C. to manufacture a functional radiant heating system.

In the following test examples, tests were conducted on the photocatalytic coating composition and the radiant heating system.

TEST EXAMPLES

Test Example 1

Ability to Decompose Organic Substances Under Visible Light Irradiation

Figure 2:
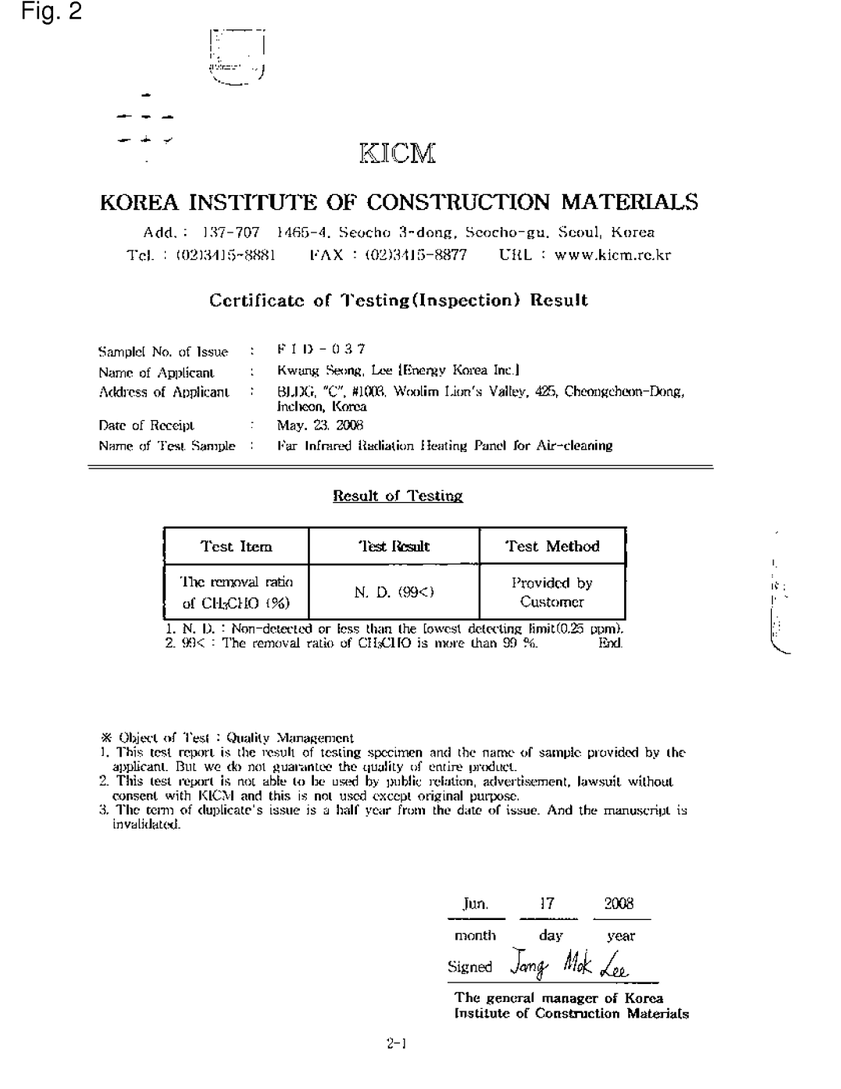
FIG. 2 is a test report showing the removal ratio of acetaldehyde of a composition according to the present invention under visible light irradiation.
Figure 3:
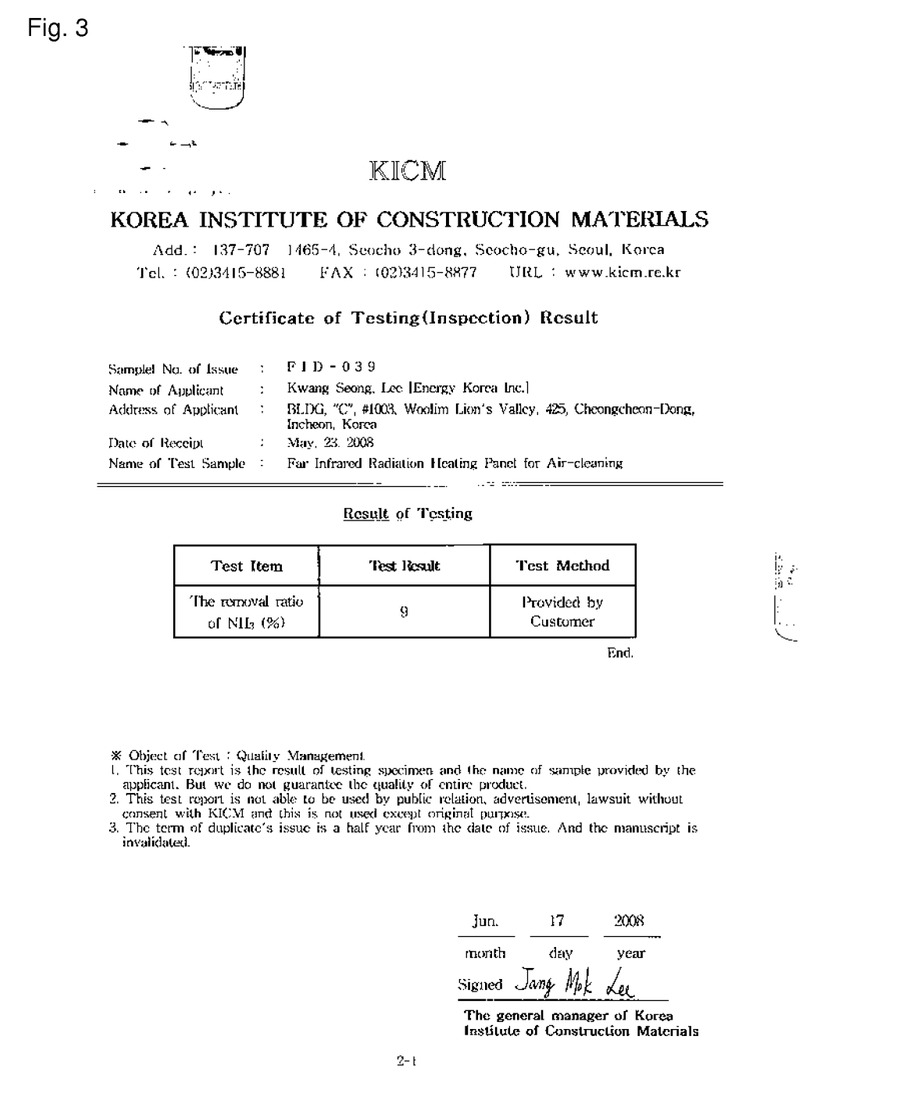
FIG. 3 is a test report showing the removal ratio of ammonia of a composition according to the present invention under visible light irradiation.

The photocatalytic coating composition was dried and pulverized. The powder was used as a sample to measure the removal ratios of $CH_3CHO$ and $NH_3$. The tests were conducted in the Korea Institute of Construction Materials (KICM), which is an authorized testing organization in Korea. The test reports are shown in FIGS. 2 and 3.

1. Conditions and Method of Test for Removal Ratio of $CH_3CHO$

1) Manufacture of test pieces: 0.5 g of the sample was coated on respective aluminum plates and dried in air for 24 hours to manufacture test pieces.

2) Irradiation conditions of lamps: Two triple wavelength fluorescent lamps (Philips FL20SS/18 Super80) were installed at a distance of 10 cm from each of the test pieces.

3) Pretreatment for test pieces: The test pieces were not pretreated, but exposed to UV light for 3 hours.

4) Test procedure

Four pieces of 5 l PVF resin gasbags (Tokyo Deodorant Inc., Japan) were prepared. The test pieces were put in the gasbags. 3 l of 90 ppm $CH_3CHO$-air mixed gas was blown in each gasbag and sealed.

Two of the gasbags were exposed in the condition of light irradiation and the others were laid in the dark condition.

The $CH_3CHO$ concentrations in the gasbags were measured using a gas detector tube.

2. Conditions and Method of Test for Removal Ratio of $NH_3$

The test conditions and method for removal ratio of $NH_3$ were the same as those for removal ratio of $CH_3CHO$.

3. Test Results

The test results are shown in Table 1.

TABLE 1

| | Visible light (%) |
|---|---|
| $CH_3CHO$ | N.D. (99<) |
| $NH_3$ | 9 |

*Note
N.D.: $CH_3CHO$ was not detected or detected at a concentration less than the lowest detection limit (0.25 ppm) after visible light irradiation for 2 hours
99<: The removal ratio of $CH_3CHO$ was more than 99%

The removal ratio of $CH_3CHO$ was more than 99% and that of $NH_3$ was 9%, under visible light irradiation. The removal ratio of $NH_3$ was much lower than that of $CH_3CHO$. However, taking into consideration the fact that the binding force between the elements of the nitride is stronger than that between the elements of acetaldehyde, the removal ratio of $NH_3$ is evaluated to be high under visible light, which has a lower energy than UV light.

Test Example 2

Ability to Decompose Organic Substances Under UV Irradiation

Figure 4:
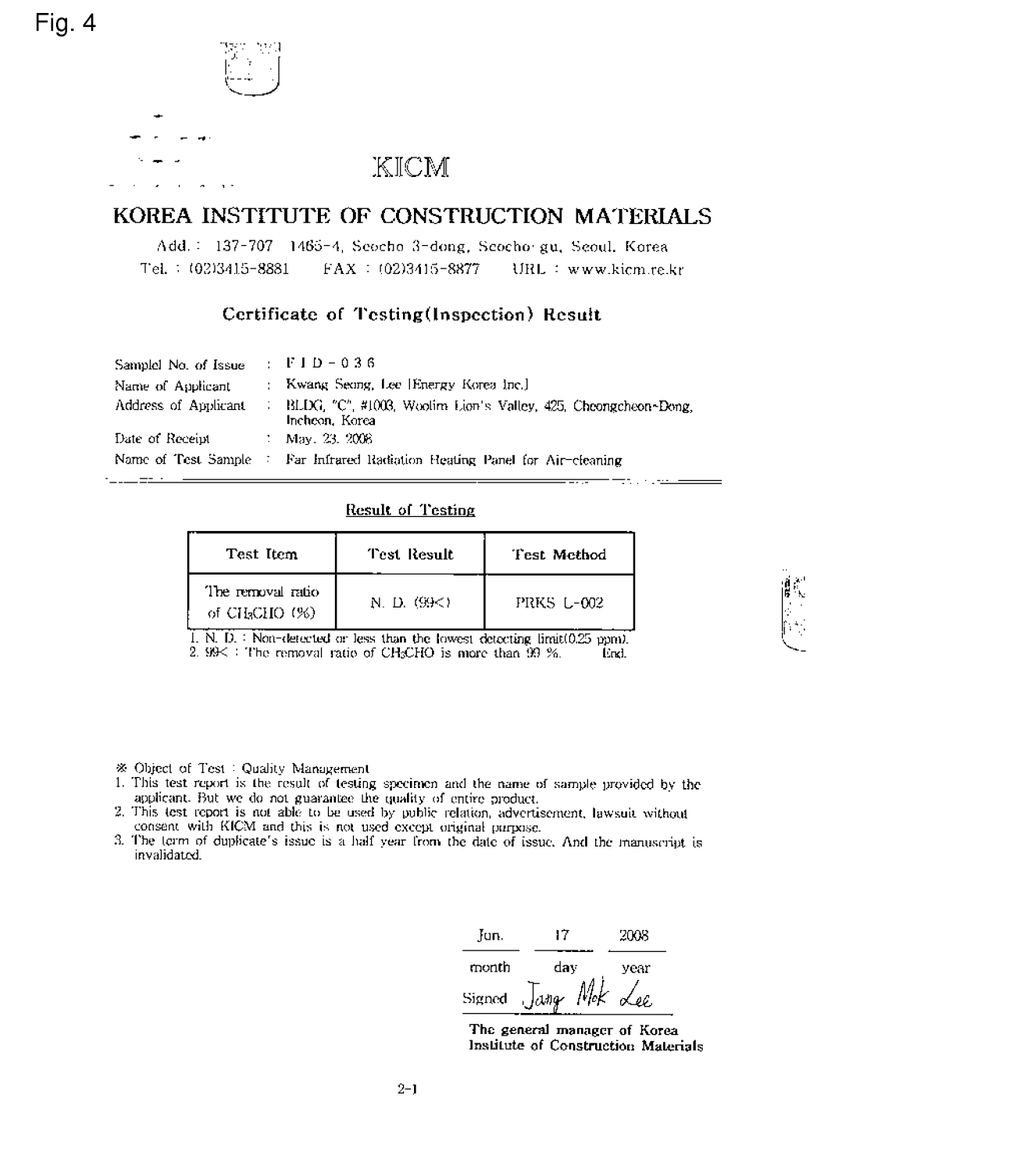
FIG. 4 is a test report showing the removal ratio of acetaldehyde of a composition according to the present invention under UV irradiation.
Figure 5:
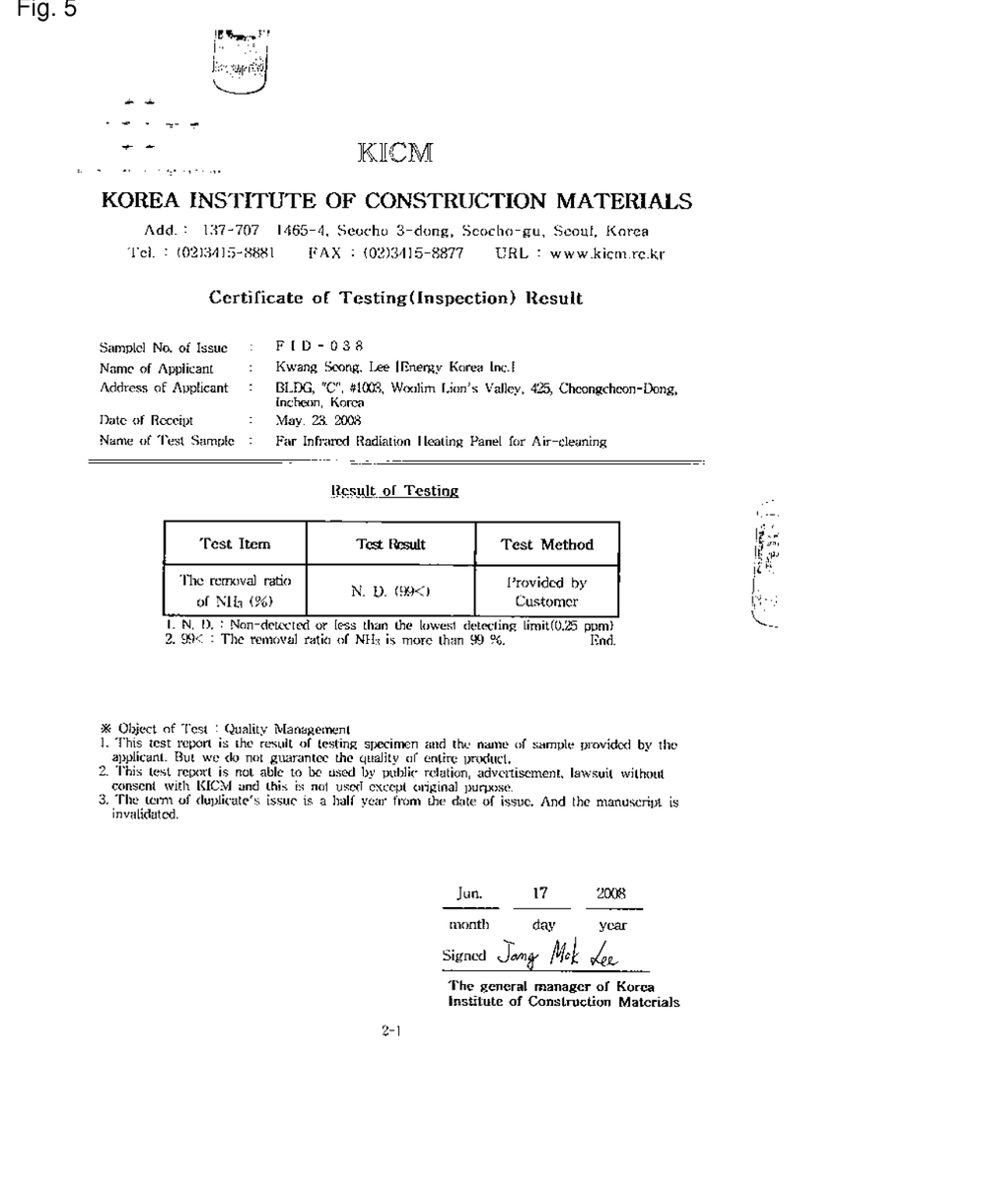
FIG. 5 is a test report showing the removal ratio of ammonia of a composition according to the present invention under UV irradiation.
Figure 6:
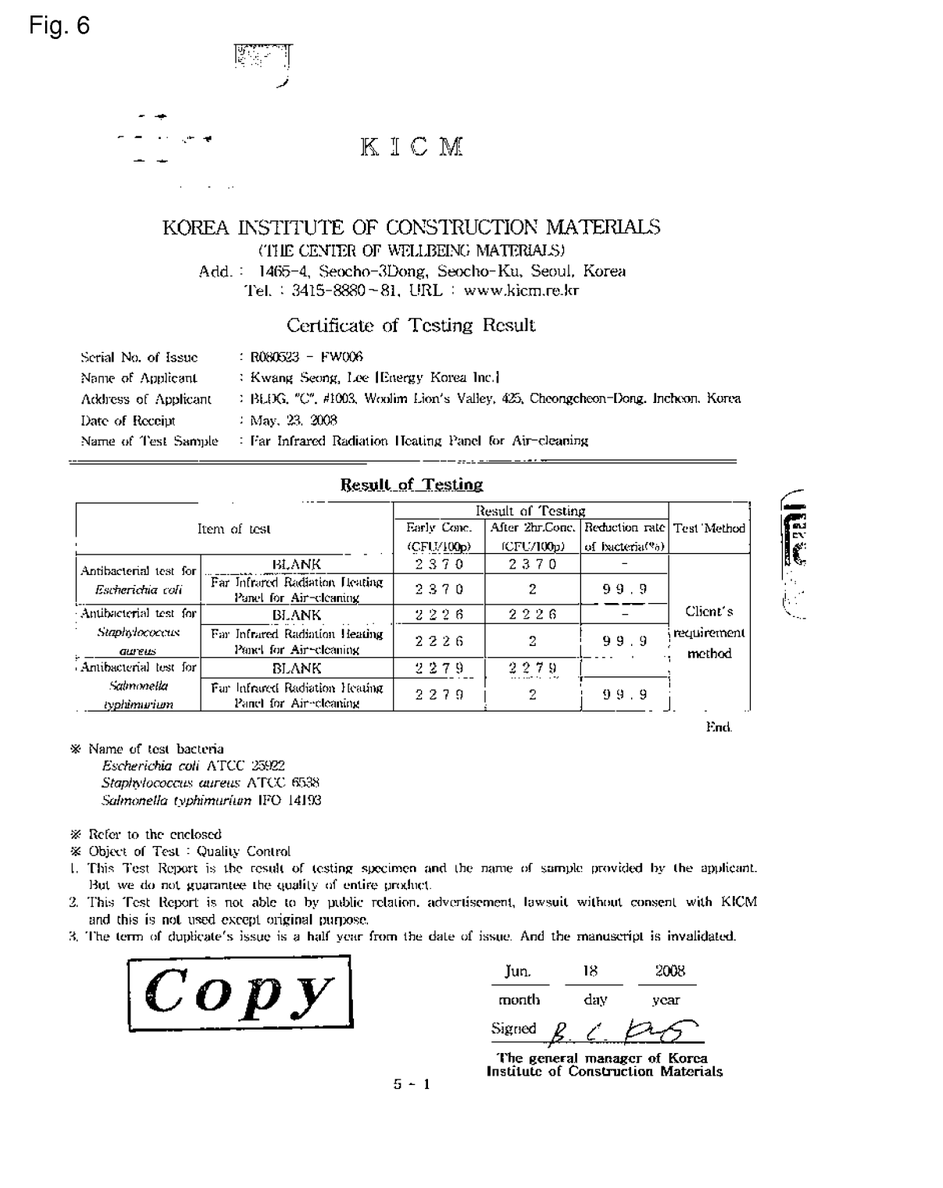
FIG. 6 is a test report showing the antibacterial activity on *Escherichia coli*, *Staphylococcus aureus* and *Salmonella typhimurium*.
Figure 7:
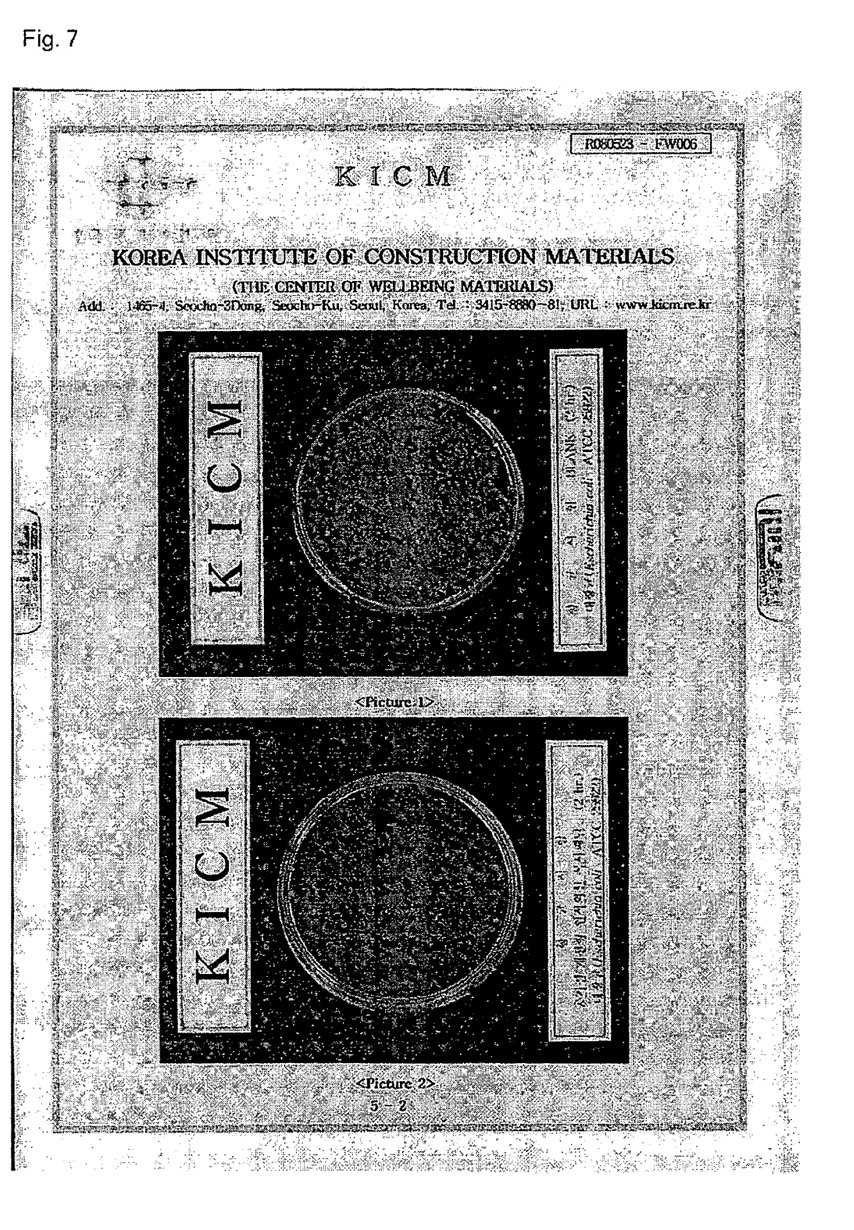
FIG. 7 shows images illustrating the antibacterial activity on *Escherichia coli* attached in the test report of FIG. 6.
Figure 8:
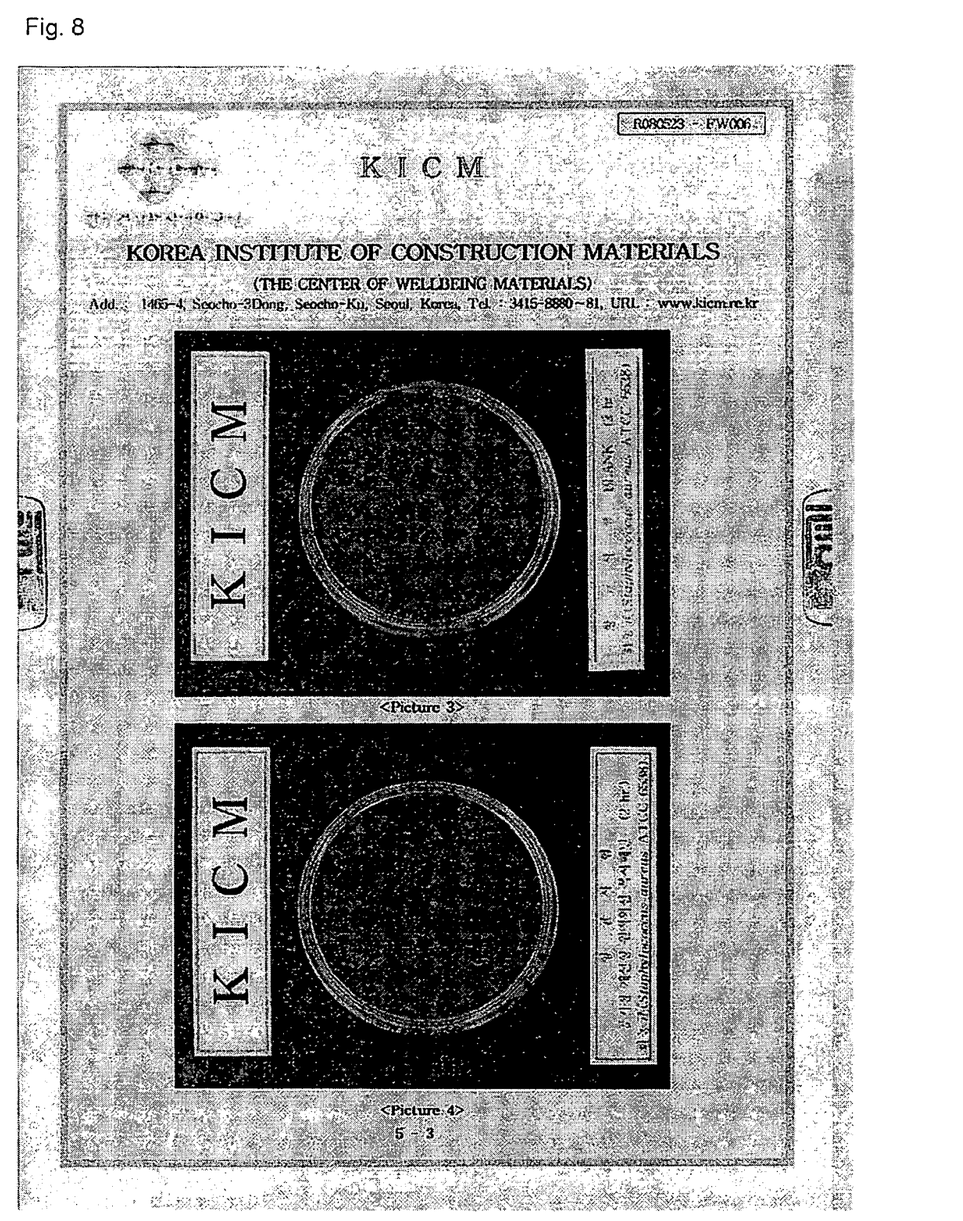
FIG. 8 shows images illustrating the antibacterial activity on *Staphylococcus aureus* attached in the test report of FIG. 6.
Figure 9:
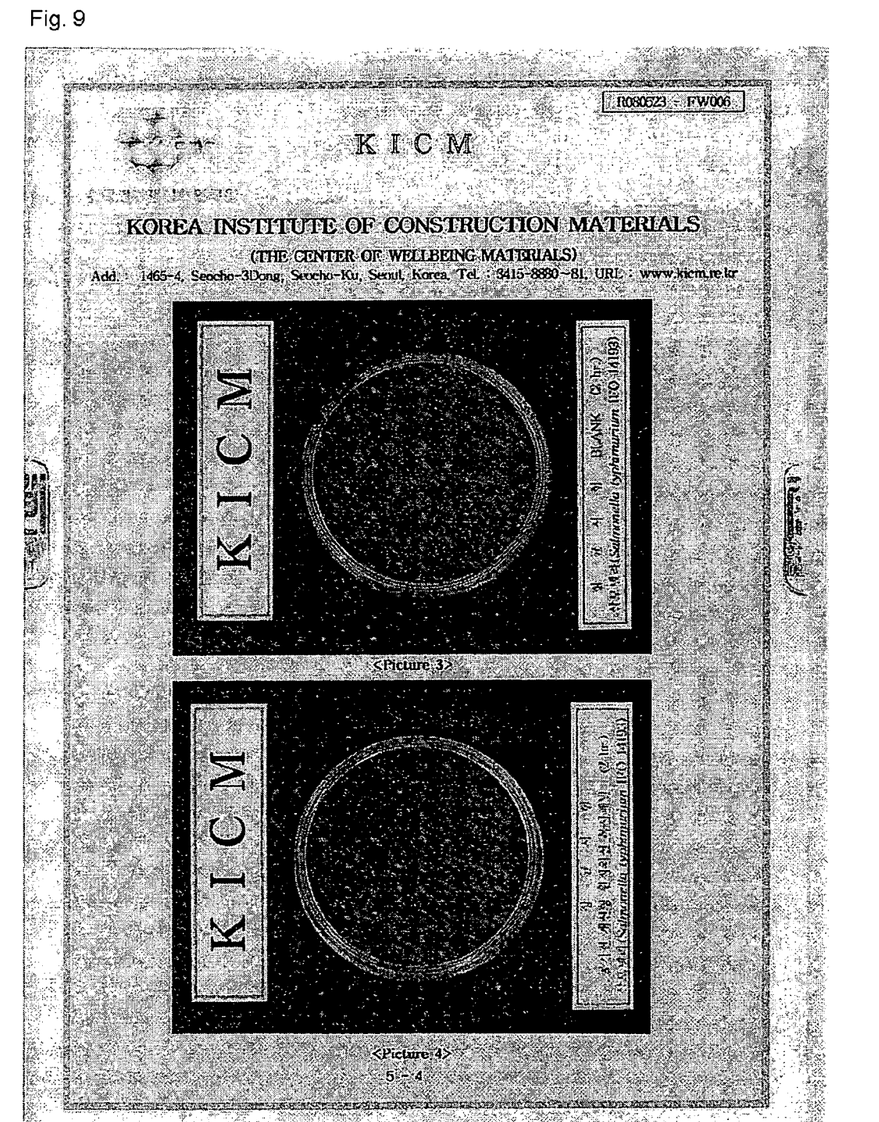
FIG. 9 shows images illustrating the antibacterial activity on *Salmonella typhimurium* attached in the test report of FIG. 6.

The photocatalytic coating composition was dried and pulverized. The powder was used as a sample to measure the removal ratios of $CH_3CHO$ and $NH_3$. The tests were conducted in the Korea Institute of Construction Materials (KICM), which is an authorized testing organization in Korea. The test reports are shown in FIGS. 4 and 5.

1. Conditions and Method of Test for Removal Ratio of $CH_3CHO$
   1) Test method: PRKS L-002 (Gasbag A method)
   2) Conditions of test
   Number and maker of blacklight fluorescent lamps: 2 and Sankyo denki
   Maker and model of UV radiation meter: Konica Minolta (UM-10), UD-360
   Test piece: 0.5 g of the sample was coated on an aluminum plate and dried in air for 24 hours to manufacture a test piece.
   Pretreatment and UV irradiation of test piece: The test piece was not pretreated, but exposed to UV light for 3 hours.
   Distance from the test piece to the UV lamps: 10 cm
   Temperature within the laboratory: 22° C.
   Confirmation of test:
   PRKS L-002: Acetaldehyde concentration within gasbags in the dark condition was not changed $$\frac{\text{(The maximum gas concentration at beginning)} - \text{(Gas concentration at beginning)}}{\text{Numerical mean concentration}} = 0$$

2. Conditions and Method of Test for Removal Ratio of $NH_3$
   1) Manufacture of test pieces: 0.5 g of the sample was coated on respective aluminum plates and dried in air for 24 hours to manufacture test pieces.
   2) Irradiation conditions of lamps: Black-light fluorescent lamps (Sankyo denki, 20 W) were installed and the UV light intensity was adjusted to 1.0 $mW/cm^2$ using a UV radiation meter (Konica Minolta, UD-360).
   3) Pretreatment for test pieces: The test pieces were not pretreated, but exposed to UV light for 3 hours.
   4) Test procedure
   Four pieces of 5 l PVF resin gasbags (Tokyo Deodorant Inc, Japan) were prepared. The test pieces were put in the gasbags. 3 l of 90 ppm $NH_3$-air mixed gas was blown in each gasbag and sealed.
   Two of the gasbags were exposed in the condition of light irradiation and the others were laid in the dark condition.
   The $NH_3$ concentrations in the gasbags were measured using a gas detector tube.

3. Test Results

The test results are shown in Table 2.

TABLE 2

|  | UV light (%) |
|---|---|
| $CH_3CHO$ | N.D. (99<) |
| $NH_3$ | N.D. (99<) |

*Note
N.D.: $CH_3CHO$ (or $NH_3$) was not detected or detected at a concentration less than the lowest detection limit (0.25 ppm) after UV irradiation for 2 hours
99<: The removal ratio of $CH_3CHO$ (or $NH_3$) was more than 99%

The removal ratios of $CH_3CHO$ and $NH_3$ were more than 99%.

Test Example 3

Tests for Antibacterial Effects

Antibacterial tests were conducted on *Escherichia coli, Staphylococcus aureus* and *salmonella typhimurium* in the Korea Institute of Construction Materials (KICM), which is an authorized testing organization in Korea. The test report are shown in FIGS. 6 through 9.

1. Conditions and Method of Test
   1) Irradiation conditions of lamps: Two three-wavelength fluorescent lamps (Philips FL20SS/18 Super80) were installed at a distance of 10 cm from test pieces.
   2) After inoculation of a bacterial solution, the test pieces were exposed to the fluorescent lamps for 2 hours.
   3) The samples were placed in respective Petri dishes, and the bacterial solution was inoculated thereinto. The Petri dishes were exposed to the fluorescent lamps for 2 hours and washed with a buffer. The number of the remaining bacteria was counted.
   4) Name of test bacteria
   *Escherichia coli* (ATCC 25922)
   *Staphylococcus aureus* (ATCC 6538)
   *Salmonella typhimurium* (IFO 14193)
   5) Sample size: 5×5 cm 2. Test Results The test results are shown in Table 3.

TABLE 3

| Bacterial Strains | Early concentration (CFU/100 p) | Concentration after 2 hr (CFU/100 p) | Antibacterial performance (Reduction rate (%) of bacteria) |
|---|---|---|---|
| *Escherichia coli* (ATCC 25922) | 2,370 | 2 | 99.9 |
| *Staphylococcus aureus* (ATCC 6538) | 2,226 | 2 | 99.9 |
| *Salmonella typhimurium* (IFO 14193) | 2,279 | 2 | 99.9 |

The reduction rates were all 99.9% for *Escherichia coli* (ATCC 25922), *Staphylococcus aureus* (ATCC 6538) and *Salmonella typhimurium* (IFO 14193).

Test Example 4

Far-Infrared Emissivity of Radiant Heating System and Adhesion of Photocatalyst

Figure 10:
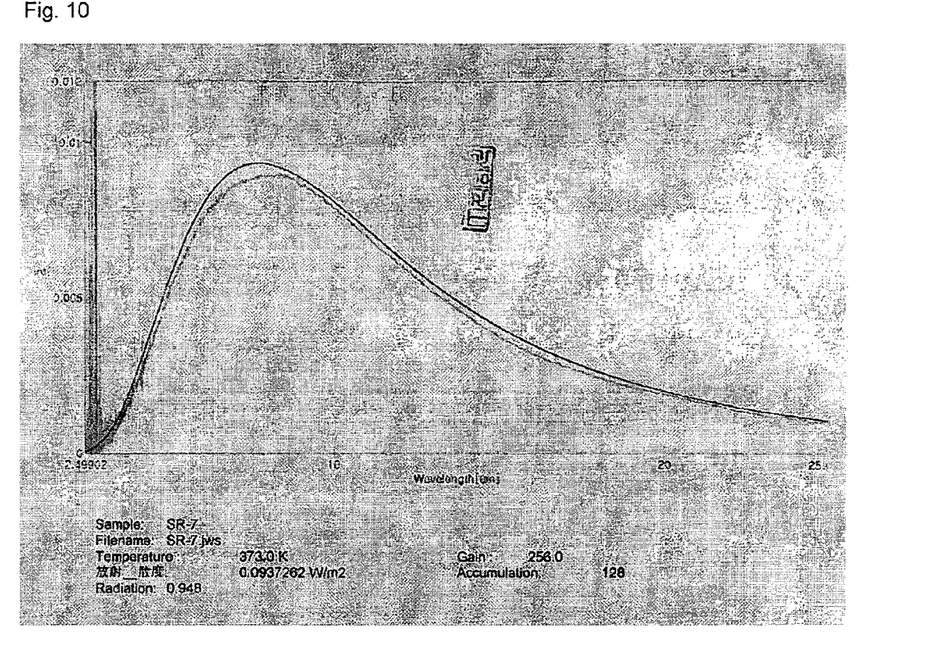
FIG. 10 is a graph showing the far-infrared emissivity of a radiant heating system comprising a photocatalytic coating composition of the present invention.

A test was conducted for far-infrared emissivity of the radiant heating system. The test was conducted in the Korea Institute of Energy Research (KIER), which is an authorized testing organization in Korea. The test report is shown in FIG. 10.

1. Conditions and Method of Test (1) Far-Infrared Emissivity

The radiant heating system and a black body were tested for far-infrared emissivity using an FT-IR spectrometer in the Korea Institute of Energy Research (KIER).

(2) Adhesion of Photocatalytic Coating Material

An adhesive tape was attached to and removed from the surface of the radiant heating system. The tape was made of propylene/rubber and had a tensile strength of 6.8 Kg/in (ASTM Test Methods D-3652, D-3652, D-3330, D-3759 and D-3759).

2. Test Results

The test results are shown in Table 4.

TABLE 4

| Far-infrared emissivity | Adhesiveness |
|---|---|
| 94.8% | No peeling was observed |

The far-infrared emissivity of the radiant heating system was high (94.8%) and no peeling of the photocatalytic composition was observed.

INDUSTRIAL APPLICABILITY

As apparent from the foregoing, the photocatalytic coating composition of the present invention exhibits high photocatalytic activity even in the visible region and is thus applicable to interior products as well as exterior products.

In addition, no separation of a photocatalyst is observed in the photocatalytic coating composition of the present invention with the passage of time.

Furthermore, the radiant heating system of the present invention comprises a coating layer having the photocatalytic coating composition to have the ability to purify indoor air.

The invention claimed is:

1. A photocatalytic coating composition comprising 5 to 20% by weight of a hydroxyapatite-coated photocatalyst, 5 to 15% by weight of a silica-based binder, 1 to 5% by weight of an acrylic emulsion, 0.1 to 1% by weight of a thickener and 64 to 85% by weight of water;

wherein the particles of the hydroxyapatite-coated photocatalyst have a hydroxyapatite grown onto the surface thereof having a coverage ratio in the range of 5 to 36%.

2. The composition according to claim 1, characterized in that the hydroxyapatite coated photocatalyst has an average particle diameter in the range of 1 to 250 nm.

3. The composition according to claim 1, characterized in that the photocatalyst is selected from titanium dioxide, zinc oxide, zirconium oxide, tin oxide, vanadium trioxide and combinations thereof.

4. The composition according to claim 1, characterized in that the thickener is xanthan gum.

\* \* \* \* \*